United States Patent [19]
Bencsits

[11] Patent Number: 5,594,029
[45] Date of Patent: Jan. 14, 1997

[54] USE OF FIRST RUNNINGS COCONUT FATTY ACID AS INSECT-REPELLENT

[75] Inventor: Franz Bencsits, Wehrenbachhalde 54, 8053 Zürich, Switzerland

[73] Assignees: Franz Bencsits; Perycut-Chemie AG, both of Zurich, Switzerland

[21] Appl. No.: 379,567

[22] Filed: May 11, 1995

[30] Foreign Application Priority Data

Aug. 11, 1992 [DE] Germany ..................... 42 26 581.9

[51] Int. Cl.$^6$ .................. A61K 31/23; A61K 31/19; A61K 35/60; A61K 35/12
[52] U.S. Cl. .............. 514/552; 514/557; 424/522; 424/523; 424/526; 424/DIG. 10
[58] Field of Search ................... 514/552, 557; 424/522, 523, 526, DIG. 10

[56] References Cited

U.S. PATENT DOCUMENTS 1,589,866  6/1926  Siegler et al. .
2,396,012  3/1946  Jones et al. .
3,668,226  6/1972  Quintana et al. .
4,518,593  5/1985  Juvin et al. .

FOREIGN PATENT DOCUMENTS

4012224A1  10/1991  Germany .

OTHER PUBLICATIONS

"Human Skin–Surface Lipid Fatty Acids—Mosquito Repellents,", Experientia, W. A. Skinner et al., 26(7):728–730 (1970).

"Field Studies of the Responses of Tsetse Files (Glossinidae) and Other Diptera to Carbon Dioxide, Acetone and Other Chemicals", Database Chemabs Chemical Abstracts Service, G. A. Vale, AN: CA94(17)134074b abstract and Bull. Entomol. Res. 70(4):563.–570 (1980).

"Laboratory Evaluations of Materials as Repellents for the Face Fly", Journal of Economic Entomology, Bodenstein et al., 63(6):1752–1755 (1970).

"Fatty Acids As Oviposition Repellents For Mosquitoes", Database Chemabs Chemical Abstracts Service, Y. S. Hwang et al., AN: CA97(15):122022q abstract and Proc. Pap. Annu. Conf. Calif. Mosq. Vector Control Assoc., 49th., pp. 106–107 (1982).

*Primary Examiner*—John W. Rollins
*Attorney, Agent, or Firm*—Finnegan, Henderson, Farabow, Garrett & Dunner

[57] ABSTRACT

The present invention relates to the use of natural or synthetic first runnings coconut fatty acid as an insect-repellent agent which is applied to human or animal skin or to clothing.

7 Claims, No Drawings

USE OF FIRST RUNNINGS COCONUT FATTY ACID AS INSECT-REPELLENT

DESCRIPTION

The present invention relates to the use of first runnings coconut fatty acid for repelling flying, biting or sucking insects.

Repellents are chemical substances having a repellent effect on insects. Their use in human or veterinary hygiene where they protect man and animal against attacks by bloodsucking, biting or other pestilent insects is of great importance in practice. Repellents which are to be applied directly to the skin must be non-irritating, non-poisonous, perspiration-resistant and light-fast and perfect from a cosmetic point of view. Moreover, the protection of the treated skin parts should last as long as possible and the spectrum of activity of the repellents should be as broad as possible, i.e., they should act against the largest possible number of harmful or pestilent insects.

In the past, essential oils, such as citronella oil, camphor or eucalyptus oil, were used as repellents; however, due to their disadvantages, they were predominantly replaced by synthetic repellents. Synthetic repellents used in the prior art are, for instance, phthalic acid dimethyl ester, 1,2-ethyl-hexane-1,3-diol, 3,4-dihydro-2,2-dimethyl-4-oxo-2H-pyran-6-carboxylic acid-n-butyl ester, succinic acid dipropyl ester, N,N-diethyl-3-methyl-benzoic amide and pyridine-2, 5-dicarboxylic acid-di-n-propyl ester (Ullmanns Encyklopädie der technischen Chemie, 4th edition, Vol. 13, page 237 et seq., 1977). However, it often happens that such synthetic repellents are not perspiration-resistant and irritate the mucous membranes. With each synthetic repellent, it must first of all be checked whether it is non-irritating and, recently, whether it is biodegradable.

It is therefore the object of the present invention to provide an insect-repellent agent for application to the skin on the basis of natural or pseudonatural raw materials with the least toxicological risk, which also exhibits high efficiency over a long period of time.

This object is attained according to the invention by the use of a natural or synthetic first runnings coconut fatty acid as an insect-repellent agent.

If the first runnings coconut fatty acid used according to the invention is present in an insect-repellent, it may have added as another active substance an oil or fat selected from the group consisting of rape-seed oil, sunflower oil, peanut oil/butter, soy oil, safflower seed oil, cuphea oil, coconut oil, palm kernel oil, palm oil, beef tallow, pig fat, mutton fat and fish oil.

A natural, pseudonatural or synthetic fatty alcohol having preferably 5 to 18 carbon atoms, which is saturated or has 1 to 3 unsaturated bonds per molecule, may be added as another active substance. The natural fatty alcohols are, for instance, obtained from vegetable and/or animal oils and/or the fatty acids and/or fatty acids alkyl esters obtainable therefrom. The pseudonatural and/or synthetic fatty alcohols can, for instance, be obtained from paraffin and/or ethene.

An insect-repellent which contains the first runnings coconut fatty acid used according to the invention alone, or also in combination with said other active substances, may be present as an aqueous emulsion, with alkyl sulfates, alkyl sulfonates, alkyl aryl sulfonates and alkoxylates of natural or synthetic origin being adapted to be used as emulsifiers.

An insect-repellent containing 5 to 99% by weight of the first runnings coconut fatty acid and 1 to 95% by weight of at least one fatty oil is especially efficient. Another insect-repellent contains 5 to 99% by weight of first runnings coconut fatty acid and 1 to 95% by weight of at least one fatty alcohol.

Furthermore, an efficient insect-repellent comprises 10 to 98% by weight of first runnings coconut fatty acid, 1 to 89% by weight of at least one fatty oil and 1 to 89% by weight of at least one fatty alcohol.

Other insect-repellents containing the first runnings coconut fatty acid used according to the invention comprise 10 to 90% by weight of first runnings coconut fatty acid, 8 to 88% by weight of at least one emulsifier and 2 to 82% by weight of water, or 8 to 89% by weight of first runnings coconut fatty acid, 1 to 79% by weight of at least one fatty oil, 8 to 88% by weight of at least one emulsifier and 2 to 82% by weight of water, or 8 to 88% by weight of first runnings coconut fatty acid, 1 to 79% by weight of at least one fatty oil, 8 to 88% of at least one emulsifier, 1 to 78% by weight of at least one fatty alcohol and 2 to 82% by weight of water.

Insect-repellents are also suited that contain 10 to 90% by weight of first runnings coconut fatty acid and 10 to 90% by weight of at least one lower alcohol having 1 to 4 carbon atoms, for instance ethyl, methyl, propyl, isopropyl or butyl alcohol, or 10 to 90% by weight of first runnings coconut fatty acid, 10 to 89% by weight of at least one lower alcohol and 1 to 80% by weight of water, or 9 to 89% by weight of first runnings coconut fatty acid, 2 to 82% by weight of at least one lower alcohol, 8 to 79% by weight of at least one emulsifier and 1 to 80% by weight of water.

The aqueous formulations of such insect-repellents preferably contain 0.001 to 15% by weight of a base, for instance sodium hydroxide, potassium hydroxide and/or triethanolamine.

The natural or synthetic first runnings coconut fatty acid used arcording to the invention can be obtained by means of a simple chemical reaction from natural or pseudonatural, toxicologically harmless raw materials, for instance by hydrolysis, transesterification, hydrogenation, high-pressure hydrogenation, hardening and/or dehydration as known in the prior art. Fatty oils possibly used in combination therewith can also be obtained in conventional processes from oil-supplying raw materials such as plant seeds and animal fats. Hence, an insect-repellent prepared from said substances contains absolutely safe synthetic (pseudonatural) or natural elements, and consequently presents the least toxicological or irritative risk together with an excellent repelling effect. The first runnings coconut fatty acid or an insect repellent containing said acid is preferably used by applying it to the skin or clothing for repelling flying, biting or sucking insects in man or animal.

The following examples will explain the invention:
1. Examples of the use of first runnings coconut fatty acid in insect-repellents (I)
30% by wt. of first runnings coconut fatty acid (C6–C12)
15% by wt. of fatty alcohol ethoxylate with 9 mole EO
55% by wt. of water (II)
30% by wt. of first runnings coconut fatty acid (C6–C12)
15% by wt. of fatty alcohol ethoxylate with 9 mole EO
10% by wt. of isopropanol
45% by wt. of water (III)
30% by wt. of first runnings coconut fatty acid (C6–C12)

15% by wt. of fatty alcohol ethoxylate with 9 mole EO

10% by wt. of isopropanol

2% by wt. of potassium hydroxide

43% by wt. of water

2. Applications

The insect repellents (II) and (III) were tested on different persons:

Test:

The forearm of a test person was treated on an area of about 250 cm$^2$ with a corresponding amount of test substance (II) and (III), respectively. An amount of 2 ml of the corresponding test substance was uniformly distributed. The treated forearm was sealed at both ends with a mosquito-tight adhesive tape and a short flexible tube of plastics. The untreated hand was covered with a thick glove, thereby serving as a control for the biting activity of the test animals at the same time.

About 300 to 400 yellow-fever mosquitos (*Aedes aegypti*), almost exclusively females, were put as test animals into a breeding cage measuring 40×40×40 cm.

The forearm and the hand were held into the mosquito cage for the test every hour, and, for 10 minutes, the number of mosquitos was recorded that (a) attempted to bite through the glove (positive control), (b) approached the treated area closer than 3 cm, (determined at the beginning, in the middle, at the end of the test), (c) remained seated on the treated area for more than 2 seconds, and (d) bit the treated area and sucked blood.

Parameters (a) and (b) are estimated values because an exact determination is not possible.

| | Test Substance (III) (Test Person (1)) | |
|---|---|---|
| Time (h) | Remaining seated (c) | Biting (d) |
| 1 | 8 | 0 |
| 2.25 | 1 | 0 |
| 3.5 | 0 | 0 |
| 4.75 | 9 | 0 |
| 6 | 0 | 0 |
| 7 | 7 | 0 |
| 8 | 3 | 0 | a) Average per test phase on the glove: 100
b) Approaching: 10-9-5

| | Test Substance (II) (Test Person (2)) | |
|---|---|---|
| Time (h) | Remaining seated (c) | Biting (d) |
| 1 | 0 | 0 |
| 2 | 0 | 0 |
| 3 | 0 | 0 |
| 4 | 0 | (2)* |
| 5 | 0 | 0 |
| 6 | 0 | 0 |
| 7 | 1 | 0 |
| 8 | 0 | 0 | a) Average per test phase on the glove: 100
b) Approaching: 1-1-1
*These two bites were made in the edge portion of the test surface, an area which was probably freed from the agent due to the protective cuff.

| | Test Substance (III) (Test Person (2)) | |
|---|---|---|
| Time (h) | Remaining seated (c) | Biting (d) |
| 1 | 0 | 0 |
| 2 | 1 | 0 |
| 3 | 0 | 0 |
| 4 | 0 | 0 |
| 5 | 0 | 0 |
| 6 | 0 | 0 |
| 7 | 1 | 0 |
| 8 | 0 | 0 | a) Average per test phase on the glove: 100
b) Approaching: 2-2-2

The efficienty of test substances (II) and (III) is excellent with respect to all parameters. Both substances show a good repelling effect over the whole test period. (Approaching mosquitos at the beginning, in the middle and at the end of the test; see detail b)). Protection against mosquito bites is excellent because none of the test persons was bitten during the whole test period which lasted for 8 h.

The efficiency of the substances results above all from the ratio of the mosquitos which remain seated on the glove and are ready to bite, to the other values. The number of biting mosquitos is a decisive factor for the duration of the effect and thus, in the tropics, indirectly also for the risk of infection. The tested substances guarantee protection for at least 8 hours. As can be seen from parameters b) and c), there is also a certain number of approaching and sitting mosquitos when the first runnings coconut fatty acid is used; these mosquitos, however, do not bite. Hence, a strong repellent effect can be attributed to all of the tested substances.

I claim:

1. A method for repelling insects from a surface comprising applying to said surface an effective amount of an insect repellent composition containing first runnings coconut fatty acid and an oil or fat selected from the group consisting of rape-seed oil, sunflower oil, peanut oil, peanut butter, soy oil, safflower seed oil, cuphea oil, coconut oil, palm kernel oil, palm oil, beef tallow, pig fat, mutton fat, and fish oil.

2. The method of claim 1, wherein the insect-repellent composition is applied to human or animal skin.

3. The method of claim 1, wherein the insect-repellent composition is applied to clothing.

4. The method of claim 1, wherein the insect-repellent composition contains first runnings coconut fatty acid and soy oil.

5. A method for repelling insects from a surface comprising applying to said surface an effective amount of first runnings coconut fatty acid.

6. An insect-repellent composition comprising first runnings coconut fatty acid and an oil or fat selected from the group consisting of rape-seed oil, sunflower oil, peanut oil, peanut butter, soy oil, safflower seed oil, cuphea oil, coconut oil, palm kernel oil, palm oil, beef tallow, pig fat, mutton fat, and fish oil.

7. A method for repelling insects from a surface comprising applying to said surface an effective amount of an insect-repellent composition containing first runnings coconut fatty acid and a fatty alcohol having 5 to 18 carbon atoms.

* * * * *

UNITED STATES PATENT AND TRADEMARK OFFICE
CERTIFICATE OF CORRECTION

PATENT NO. : 5,594,029
DATED : January 14, 1997
INVENTOR(S) : Franz Bencsits

It is certified that error appears in the above-indentified patent and that said Letters Patent is hereby corrected as shown below:

Title page,
Delete " [22]   Filed:   May 11, 1995" and insert therefor

--[22] PCT Filed:   Jul. 27, 1993

[86] PCT No.:   PCT/EP93/02003

§ 371 Date:   May 10, 1995

§ 102(e) Date:   May 10, 1995

[87] PCT Pub. No.:   WO 94/04029

PCT Pub. Date:   March 3, 1994--.

Signed and Sealed this

Twenty-second Day of September, 1998

Attest:

BRUCE LEHMAN

*Attesting Officer*     *Commissioner of Patents and Trademarks*